(12) United States Patent
Širek et al.

(10) Patent No.: US 6,649,792 B2
(45) Date of Patent: Nov. 18, 2003

(54) METHOD OF CHEMICAL RECYCLING OF POLYETHYLENE TEREPHTHALATE WASTE

(76) Inventors: Milan Širek, Malá Štěpánská 11, 120 00, Praha 2 (CZ); Jaroslav Jiroušek, 398 48, Jetětice 88 (CZ)

( * ) Notice: Subject to any disclaimer, the term of this patent is extended or adjusted under 35 U.S.C. 154(b) by 0 days.

(21) Appl. No.: 10/221,502
(22) PCT Filed: Mar. 8, 2001
(86) PCT No.: PCT/CZ01/00015
§ 371 (c)(1), (2), (4) Date: Sep. 13, 2002
(87) PCT Pub. No.: WO01/68581
PCT Pub. Date: Sep. 20, 2001

(65) Prior Publication Data
US 2003/0032840 A1 Feb. 13, 2003

(30) Foreign Application Priority Data
Mar. 17, 2000 (CZ) ........................................ PV 2000-969

(51) Int. Cl.$^7$ ............................. C07C 51/09; C07C 27/02
(52) U.S. Cl. ........................................ 562/483; 568/858
(58) Field of Search ........................ 562/483; 568/858, 568/400

(56) References Cited

U.S. PATENT DOCUMENTS 4,542,239 A * 9/1985 Lamparter et al. .......... 562/487
4,605,762 A    8/1986 Mandoki
5,328,982 A * 7/1994 Tindall et al. ............... 528/488

FOREIGN PATENT DOCUMENTS

WO         9527753      10/1995

OTHER PUBLICATIONS

Derwent Pub. 199616, AN–1996–155970 XP 002179415 of JP 08 039562 A, Feb. 13, 1996 (Mitsubishi Jukogyo kk).
Derwent Pub. 199927, AN–1999–322106, XP 002179416 of JP 11 114961, Apr. 27, 1999 (Seishin Kigyo kk).

* cited by examiner

Primary Examiner—Alan L. Rotman
Assistant Examiner—Taylor V Oh
(74) Attorney, Agent, or Firm—Dykema Gossett PLLC

(57) ABSTRACT

The proposed method of chemical recycling of polyethylene terephthalate waste to terephthalic acid and ethandiol is based on a continuous series of gradual steps, namely (a) separation of the polyethylene terephthalate component of the input material by its conversion to brittle form through crystallization, grinding and subsequent sifting, followed by (b) continuous two-stage hydrolysis of the polyethylene terephthalate, carried out in the first stage by feeding steam to the polymer melt, and in the second stage, by the reaction of the products of the first stage of hydrolysis with ammonium hydroxide, followed by (c) condensation of terephthalic acid from an aqueous solution of the second-stage hydrolysis products by inorganic acid, and its separation by means of filtration, and finally (d) rectification separation of ethandiol from a solution of the products of the second stage of hydrolysis, after the separation of terephthalic acid.

5 Claims, No Drawings

METHOD OF CHEMICAL RECYCLING OF POLYETHYLENE TEREPHTHALATE WASTE

FIELD OF THE INVENTION

The invention relates to the method of chemical recycling of polyethylene terephthalate waste to terephtalic acid and ethylene glycol.

BACKGROUND OF THE INVENTION

The polycondensation of ethylene glycol, in combination with terephthalic acid, to polyethylene terephthalate (PET) is a reversible reaction process, which makes it possible to de-polymerize PET back to monomers or oligomers. Essentially, PET de-polymerizing can be conducted in the same manner as glycolysis, hydrolysis or alcoholysis. The decomposition of PET in glycolic environment, i.e. glycolysis, is in principle based on the transesterification of the PET glycol, resulting in a mixture of aromatic polyols, which can be processed in the production of polyurethanes, or unsaturated polyester resins (U.S. Pat. Nos. 3,222,299, 4,078,143). When the input raw material for the glycolysis-type method of recycling PET waste is sufficiently pure, i.e. sorted out, washed and without admixtures of chromatic PET, the oligomeric products of this process can be used for polymerizing the new PET.

The monomers usable for polycondensation back to PET can be obtained through the process of hydrolysis or alcoholysis of PET waste. The products of PET hydrolysis include ethylene glycol and terephthalic acid, while alcoholysis results in ethylene glycol and respective esters of the terephthalic acid. The older process patented by the DuPont company (U.S. Pat. No. 3,544,622) is based on the hydrolysis of crushed PET in aqueous solution of NaOH and ethyleneglycol, at a temperature ranging from 90 to 1500 Centigrade and under atmospheric pressure, to disodium salt of terephthalic acid. The yield of disodium salt of terephthalic acid. The yield of disodium salt of terephthalic acid is 97.5%. The process developed later by the Michigan University of Technology for processing waste bottles is based on the hydrolysis of crushed PET in a surplus of water, at a temperature of from 150 to 2500 Centigrade and under increased pressure, catalyzed by sodium acetate (U.S. Pat. No. 4,542,239). Through this process, the complete decomposition of PET to ethyleneglycol and terephthalic acid is achieved within 4 hours.

A different process of neutral hydrolysis of condensation polymers is subject to U.S. Pat. No. 4,605,762. This invention essentially consists in neutral hydrolysis of condensation polymers by superheated steam. According to this invention, polyester-, polyamide- or polycarbonate based waste can be used as the input materials for this process. The hydrolytic process is conducted continuous in a pressure hydrolytic reactor at a temperature between 200 and 300° Centigrade and under pressure of minimally 1.5 MPa. The process is designed as counter-current, with the steam supplied to the bottom part of the reactor and the solution of the condensate hydrolysis product trapped in and drawn off from the reactor upper part. The thermal energy of the supplied steam is used to heat up the reactor. The input polymeric material can be pre-processed in a screw extruder and enter the hydrolytic reactor in the form of melt.

According to another invention (U.S. Pat. No. 6,031,128), terephthalic acid can be produced from PET waste using alkaline hydrolysis by waste water from the process of chromatic polyester fiber treatment. This water contains alkaline hydroxide and wetting agents.

Further inventions, mainly those of later date, concern procedures resulting in higher purity of the final product, i.e. the terephthalic acid. According to WO 95/10499, the process essentially consists in alkaline hydrolytic de-polymerization of the input polyester material. This process is improved by including an oxidation phase, preferably aeration, thus converting soluble contaminating components to insoluble ones. The insoluble oxidation products of the contaminants are subsequently removed by means of filtration. The hydrolysis stage can be further improved by adding a non-ionogenic wetting agent and quaternary ammonium hydroxide to the hydrolyzed mixture.

The process according to WO 97/24310 tackles the manner of regenerating high-purity terephthalic acid from a raw material based on PET waste. It uses alkaline hydrolysis by aqueous solution of alkaline hydroxide or alkaline earth metal hydroxide in combination with a wetting agent. Terephthalic acid is obtained from the hydrolyzate by means of its acid neutralization. Higher purity of the precipitated terephthalic acid is in this case achieved by means of controlled enlargement of the terephthalic acid particles through its crystallization.

The method of crushed PET decomposition under the effect of different alcohols was patented by Eastman Kodak in 1970 (U.S. Pat. No. 3501420). The best-suitable alcohol for PET decomposition however appears to be methanol. The methanolytic process is relatively tolerant to contamination of the input material. Chromatic PET types are no obstacle to obtaining products which are suitable for clear polymer synthesis of top quality. During a typical process of methanolysis, PET melt is mixed with methanol in a 1:4 ratio, and the mixture is heated to a temperature between 160 and 240° Centigrade under pressure of 2.0 to 7.0 MPa for a period of approximately one hour. A yield of 99% of dimethylterephthalate is reported (U.S. Pat. No. 3,403,115).

An advantage of processes based on glycolysis are relatively low investment costs, but in order to obtain raw material suitable for the polymerization of new PET, the input PET waste material needs to be highly pure and without admixtures of chromatic PET types. PET alcoholysis, on the other hand, and particularly methanolysis, while relatively tolerant to the contents of impurities in the input material, require very high investments into the necessary technological equipment.

SUMMARY OF THE INVENTION

The above-mentioned disadvantages of the actual state of technology are to a great extent eliminated by the method of chemical recycling of polyethylene terephthalate waste to terephthalic acid and ethylene glycol, as the hydrolysis of polyethylene terephthalate waste with the purpose of its de-polymerization is based, according to this invention, on crushed discarded and unsorted polyethylene terephthalate products, especially drink bottles which contain a maximum of 30% of contaminants. Essentially the process includes the following steps:

a) The first step involves separation of the polyethylene terephthalate component of the input material by its conversion to brittle form by means of crystallization, grinding and subsequent sifting. In keeping with the invention, the polyethylene terephthalate crystallization is carried out by tempering the input material to a temperature in the range of 140 to 190° Centigrade for a period of at least 25 and at most 60 minutes. The essence of the purification of the input material in this manner is the separation of the polyethylene terephthalate component, which is capable under such conditions of crystallization accompanied by its embrittlement, from the contaminants in the input mixture such as polyolefins, PVC, paper and adhesive residues which stay tough under the described conditions and resist the subsequent grinding. The ground mixture then contains fine-grained particles of polyethylene terephthalate and very coarse-grained particles of the contaminants. The ratio between medium-sized particles of the polyethylene terephthalate component and medium-sized particles of other components of the ground material is approximately 1:10. The polyethylene terephthalate component is subsequently removed from this mixture by sifting.

b) The next step consists of continuous two-stage hydrolysis of the polyethylene terephthalate, conducted in the first stage by feeding steam to the polymer melt in the extrusion reactor. The reactor is composed of a double-screw extruder, with the length of the screws representing at least 25-times their diameter (L/D≧25), and a follow-up static mixer at its outlet. The products of the first stage of hydrolysis are carried away from the extrusion reactor outlet to the second-stage reactor, where they react with the surplus of the aqueous solution of ammonium hydroxide, resulting in terephthalic acid ammonium salt and ethylene glycol. Admixtures insoluble in water are removed from the solution of the products of the second stage of hydrolysis by means of filtration.

c) The following step involves terephthalic acid condensation (precipitation) from the aqueous solution of the products of the second stage of hydrolysis by means of an inorganic acid, and its separation by filtration.

d) In the final step, ethylene glycol is separated from the filtrate of the second-stage hydrolysis products, after the separation of terephthalic acid by means of continuous two-stage rectification.

The advantages of this invention, comparing with the PET waste recycling methods known so far, are the following:

1. High effectiveness of the separation of contaminating admixtures from the input material in the solid phase as described in step (a), making it possible to separate through different procedures such uneasily separable admixtures as PVC, non-crystallizing PET copolymers and residues of polymeric adhesives, while at the same time preserving the technological simplicity of the process.
2. Lower investment requirements of the polyethylene terephthalate hydrolysis as described in step (b), comparing with classical methods of hydrolysis which make use of batch pressure reactors.
3. High effectiveness and technological simplicity of the purification of hydrolysis products as described in step (b), facilitated by their solubility in water.
4. The possibility to process strongly contaminated input material of polyethylene terephthalate waste, while reaching high purity of the final products of terephthalic acid and ethylene glycol recycling.

DESCRIPTION OF THE PREFERRED EMBODIMENT

The unsorted crushed material of discarded drink bottles, with medium particle size of ca 10 mm and 24%-contents of mass admixtures, mainly polyolefins from the caps, paper and adhesives from the labels and PVC from other sorts of bottles, as well as aluminium from the bottle caps, are tempered in a tunnel furnace equipped with a screw feeder to a temperature of 175° Centigrade, while the material is retained in the furnace for 32 minutes. At the furnace outlet, the material is air-cooled to 40° Centigrade and transported by means of a pneumatic pipe conveyor to a roller mill where it is ground. A fraction with particle size less than 0.7 mm is separated from the ground mixture by sifting on a Wilfley table. In the course of this operation, the polyethylene terephthalate component of the input material is separated from the coarsest impurities which have not become embrittled and passed through the grinding stage with only a minimum change of particle size. The ground input material, purified by sifting, is pneumatically carried on to the charging hopper of the extrusion reactor. The extrusion hydrolytic reactor is composed of a double-screw extruder of an 80-mm screw diameter and length-to-screw diameter ratio L/D=25, and a static mixer which directly follows up the extruder exit. The static mixer is designed as a cylinder with a continuous axisymmetric cavity 80 mm in diameter and 800 mm in length, filled with 6 static mixing segments shaped as right-hand alternating with left-hand helices, 40 mm wide and 8 mm thick. The extruder roller is tempered in five zones to temperatures (in the direction from the hopper to the mouth) 270/280/300/300/300° Centigrade.

The static mixer jacket is tempered to 300° Centigrade. Steam feeding under 3.8 MPa pressure takes place at the end of the $1^{st}$ third of the extruder length. The extruder screws rotate at a speed of 16 revolutions per minute. A further feed of steam under the same pressure is brought to the static mixer inlet. Hydrolytic polymer decomposition, autocatalyzed by the products being formed, takes place in the course of the extrusion of the polyethylene terephthalate material. Filtration equipment is mounted onto the extrusion reactor outlet, to remove residual solid impurities from the oligomeric products of the first stage of hydrolysis. The products of the first stage of hydrolysis are fed into a stirred flow reactor for the second stage of hydrolysis. Hydrolitic reaction of oligomeric products of the first hydrolysis stage with the surplus of the aqueous solution of ammonium hydroxide takes place in this reactor at a temperature of 200° Centigrade and under 2.1 MPa pressure. The products of the second stage of hydrolysis, i.e., the aqueous solution of terephthalic acid ammonium salt and ethylene glycol, is cooled to 95° Centigrade and brought to the stirred reactor for terephthalic acid acidic precipitation. In this reactor, terephthalic acid is precipitated from the hydrolyzate by means of sulfuric acid solution. The resultant suspension is transported to a vacuum drum filter, where terephthalic acid is filtered off and washed as the final product. The filtrate containing ethylene glycol is lead away to a two-stage rectification column, where ethylene glycol is isolated from the aqueous solution as the second final product.

FIELD OF THE APPLICATION

The presented method of chemical recycling of polyethylene terephthalate waste to terephthalic acid and ethylene glycol is usable for chemical recycling of waste mixtures of polyethylene terephthalate products, especially drink bottles, packaging foils and photographic film containing up to 30% of contaminating admixtures, to monomeric materials suitable for polycondensation to new polyethylene terephthalate materials (PET).

What is claimed is:
1. (Original/Currently amended) The method of chemical recycling of polyethylene terephthalate waste to terephthalic acid and ethylene glycol with the hydrolysis of polyethylene terephthalate waste, the purpose being its depolymerization, which consists of a continuous series of repeated steps, of (a) separation of the polyethylene terephthalate component of the input material by its conversion to brittle form through crystallization, grinding and subsequent sifting, followed by (b) continuous two-stage hydrolysis of the polyethylene terephthalate, carried out in the first stage by feeding steam to the polymer melt, and in the second stage, by the reaction of the products of the first stage of hydrolysis with ammonium hydroxide, followed by (c) precipitation of terephthalic acid from an aqueous solution of the second-stage hydrolysis products by an inorganic acid which is chemically stronger than terephthalic acid, and its separation by means of filtration, and finally (d) rectification separation of ethylene glycol from a solution of the products of the second stage of hydrolysis, after the separation of terephthalic acid.

2. The method of chemical recycling according to claim 1, wherein the crystallization of the polyethylene terephthalate component of the input material in step (a) of the process being is carried out by tempering the input material to a temperature in the range of 140 to 190° Centrigrade for a period of 15 to 60 minutes.

3. The method of chemical recycling according to claim 1, wherein the first stage of polyethylene terephthalate hydrolysis in step (b) of the process is carried out by means of reactive extrusion in an extrusion reactor which consists of a double-screw extruder, with the screw length representing at least 25-times their diameter (L/D$\geqq$25), and a follow-up static mixer at the reactor outlet.

4. The method of chemical recycling according to claim 1, wherein the products of the first stage of hydrolysis in step (b) of the process are delivered from the extrusion reactor outlet to a second-stage reactor where they react with the surplus of ammonium hydroxide aqueous solution, resulting in terephthalic acid and ethylene glycol.

5. The method of chemical recycling according to claim 1, characterized by the fact that wherein said inorganic acid in step (c) is selected from the group consisting of hydrochloric acid, phosphoric acid and sulfuric acid.

* * * * *